US008871697B2

(12) United States Patent
Vedantam et al.

(10) Patent No.: US 8,871,697 B2
(45) Date of Patent: Oct. 28, 2014

(54) FRAGRANCE DELIVERY

(75) Inventors: Venkateswara Kumar Vedantam, Jalan Lempeng (SG); Tee Yong Tan, Singapore (SG)

(73) Assignee: Givaudan SA, Vernier (CH)

( * ) Notice: Subject to any disclaimer, the term of this patent is extended or adjusted under 35 U.S.C. 154(b) by 181 days.

(21) Appl. No.: 12/879,340

(22) Filed: Sep. 10, 2010

(65) Prior Publication Data

US 2011/0003731 A1 Jan. 6, 2011

Related U.S. Application Data

(63) Continuation of application No. 10/549,509, filed as application No. PCT/CH2004/000103 on Feb. 26, 2004, now abandoned.

(30) Foreign Application Priority Data

Mar. 19, 2003 (GB) .................................. 0306152.0

(51) Int. Cl.

*A61K 8/02* (2006.01)
*C11D 3/50* (2006.01)
*C11D 3/12* (2006.01)
*C11D 3/04* (2006.01)

(52) U.S. Cl.

CPC ................ *C11D 3/046* (2013.01); *C11D 3/505* (2013.01); *C11D 3/124* (2013.01)
USPC ................ 510/101; 510/349; 510/441; 512/4

(58) Field of Classification Search

USPC ............................... 510/101, 349, 441; 512/4
See application file for complete search history.

(56) References Cited

U.S. PATENT DOCUMENTS

| | | | | | |
|---|---|---|---|---|---|
| 3,898,039 | A | * | 8/1975 | Lin | 422/125 |
| 4,339,356 | A | * | 7/1982 | Whyte | 512/4 |
| 4,391,727 | A | * | 7/1983 | Benz | 252/186.3 |
| 4,539,135 | A | * | 9/1985 | Ramachandran et al. | 510/349 |
| 5,041,421 | A | * | 8/1991 | King | 512/4 |
| 5,648,328 | A | * | 7/1997 | Angell et al. | 510/441 |
| 5,656,584 | A | * | 8/1997 | Angell et al. | 510/441 |
| 5,840,668 | A | * | 11/1998 | Behan et al. | 510/112 |
| 6,113,655 | A | * | 9/2000 | Tsunetsugu et al. | 8/137 |
| 6,225,462 | B1 | * | 5/2001 | Berry et al. | 536/123.1 |
| 7,291,187 | B2 | * | 11/2007 | Welch et al. | 44/275 |
| 2002/0010108 | A1 | * | 1/2002 | Noda et al. | 510/101 |
| 2002/0016269 | A1 | * | 2/2002 | Noda et al. | 510/101 |
| 2003/0064336 | A1 | * | 4/2003 | Welch et al. | 431/288 |
| 2006/0172917 | A1 | * | 8/2006 | Vedantam et al. | 512/12 |

FOREIGN PATENT DOCUMENTS

| | | | | | |
|---|---|---|---|---|---|
| GB | 2066839 | A | * | 7/1981 | C11D 3/50 |

* cited by examiner

*Primary Examiner* — Nicole M Buie-Hatcher
*Assistant Examiner* — M. Reza Asdjodi
(74) *Attorney, Agent, or Firm* — Norris McLaughlin & Marcus, P.A.

(57) ABSTRACT

A substrate such as a fabric may be provided with a fragrance during washing or rinsing process by the addition to the wash water of a free-flowing solid fragrance-providing composition that comprises a fragrance deposited on a particulate carrier along with a water soluble salt of an alkali metal or an alkaline earth metal.

18 Claims, No Drawings

FRAGRANCE DELIVERY

This application is a Continuation patent application of U.S. Ser. No. 10/549509 filed Oct. 21, 2005 now abandoned, which in turn was a filing under 35 USC 371 of PCT/CH2004/000103, filed on 26 Feb. 2004, which in turn claims the priority benefit of GB 0306152 filed 19 Mar. 2003.

This invention relates to a means of fragrance delivery in washing products.

It is desirable to deliver fragrances such as perfumes to substrates by means of their incorporation into washing products such as laundry detergents. However, many washing products contain surfactants, which form micelles in water, and, as many fragrances are hydrophobic, they tend to migrate to the micelles, rather than deposit on the substrate.

Several methods of overcoming this problem have been tried. One is to use fragrances that are not attracted more to the micelles than to the substrate. This is possible, but it restricts greatly the range of possible fragrances that can be used.

Various methods have relied on using solid carriers for fragrances. Typical examples of such carriers include inorganic particles, usually silica (both precipitated and gel-type). However, the major drawback of these methods has been the water insolubility of the carrier.

It has now been found that an inexpensive, convenient method overcomes all these disadvantages and permits the achievement of a fragrance that is delivered to the substrate. The invention therefore provides a method of preparation of a free-flowing solid fragrance-providing composition, consisting essentially of the addition of a fragrance to a particulate carrier material in the presence of a water-soluble salt of an alkali or alkaline earth metal.

The invention additionally provides a free-flowing solid fragrance-providing composition, consisting essentially of a particulate carrier on which is deposited a fragrance and a water-soluble salt of an alkali or alkaline earth metal, the composition comprising at least 60% by weight of water-soluble salt and 20% maximum by weight of particulate carrier, and the ratio of water-soluble salt to fragrance being from 20:1 to 1.5:1.

The compositions of the present invention differ considerably from known compositions, which have high proportions of particulate carrier (usually in excess of 40% by weight) and high perfume loadings (typically from 20-50% by weight of the total composition).

In this description, unless otherwise stated, the use of the singular also includes the plural. For example, "a fragrance" also comprehends the case where more than one fragrance is used.

The fragrances for use in this invention may be selected from any suitable fragrance known to the art. It is a characteristic of this invention that an unusually broad range of fragrances may be used. Examples include digeranyl succinate, dineryl succinate, geranyl neryl succinate, geranyl phenylacetate, neryl phenylacetate, geranyl laurate, neryl laurate, di(b-citronellyl) maleate, dinonadol maleate, diphenoxyanol maleate, di(3,7-dimethyl-1-octanyl) succinate, di(cyclohexylethyl) maleate, difiralyl succinate, di(phenylethyl) adipate, 7-acetyl-1,2,3,4,5,6,7,8-octahydro-1,1,6,7-tetramethyl naphthalene, ionone methyl, ionone gamma methyl, methyl cedrylone, methyl dihydrojasmonate, methyl 1,6,10-trimethyl-2,5,9-cyclododecatrien-1-yl ketone, 7-acetyl-1,1,3,4,4,6-hexamethyl tetralin, 4-acetyl-6-tert-butyl-1,1-dimethyl indane, para-hydroxy-phenyl-butanone, benzophenone, methyl beta-naphthyl ketone, 6-acetyl-1,1,2,3,3,5 hexamethyl indane, 5-acetyl-3-isopropyl-1,1,2,6-tetramethyl indane, 1-dodecanal, 4-(4-hydroxy-4-methylpentyl)-3-cyclohexene-1-carboxaldehyde, 7-hydroxy-3,7-dimethyl ocatanal, 10-undecen-1-al, isohexenyl cyclohexyl carboxaldehyde, formyl tricyclodecane, condensation products of hydroxycitronellal and methyl anthranilate, condensation products of hydroxycitronellal and indol, condensation products of phenyl acetaldehyde and indol, 2-methyl-3-(para-tert-butylphenyl)-propionaldehyde, ethyl vanillin, heliotropin, hexyl cinnamic aldehyde, amyl cinnamic aldehyde, 2-methyl-2-(para-iso-propylphenyl)propionaldehyde, coumarin, decalactone gamma, cyclopentadecanolide, 16-hydroxy-9-hexadecenoic acid lactone, 1,3,4,6,7,8-hexahydro-4,6,6,7,8,8-hexamethylcyclo-penta-gamma-2-benzopyrane, beta-naphthol methyl ether, ambroxane, dodecahydro-3a,6,6,9a-tetramethylnaphtho[2,1b]furan, cedrol, 5-(2,2,3-trimethylcyclopent-3-enyl)-3-methylpentan-2-ol, 2-ethyl-4-(2,2,3-trimethyl-3-cyclopenten-1-yl)-2-buten-1-ol, caryophyllene alcohol, tricyclodecenyl propionate, tricyclodecenyl acetate, benzyl salicylate, cedryl acetate, para-(tert-butyl)cyclohexyl acetate, essential oils, resinoids, and resins from a variety of sources including but not limited to orange oil, lemon oil, patchouli, Peru balsam, Olibanum resinoid, styrax, labdanum resin, nutmeg, cassia oil, benzoin resin, coriander, lavandin, and lavender, phenyl ethyl alcohol, terpineol, linalool, linalyl acetate, geraniol, nerol, 2-(1,1-dimethylethyl)cyclohexanol acetate, benzyl acetate, orange terpenes, eugenol, diethylphthalate, and combinations thereof.

These fragrances are generally available in liquid form (as solutions in organic solvent) and this is the form in which they are used in this invention.

The carrier material may be any suitable particulate carrier known to the art to be suitable as a carrier material for fragrances. Preferred are fine, porous silicas. Typical silicas are precipitated silicas, or they may be fumed silicas. The silicas should have a particle size 2-15 μM and a BET surface area of from 140 to 550 $M^2$/g. Preferably the silicas are capable of adsorbing from 2-3 times their weight in fragrance. Suitable silicas of the correct particle size may be provided in that size, or they may be produced from larger particle size silicas by known techniques, such as milling. Typical commercial products include SIPERNAT (trade mark) 22S, 22LS and 50S (ex Degussa). It is possible to use silica particles of other sizes and hydrophilicity, but these are less preferred.

Part of the silica can be replaced by other absorbent particulate materials, such as bentonites and cellulose derivatives (for example carboxymethyl cellulose). Up to 50% by weight can be replaced but preferably the replacement is no higher than 40%, preferably no higher than 30%.

The water-soluble salts of alkali or alkaline earth metals may be any such salts known to the art. Typical examples include sodium and potassium chlorides and sodium sulphate, sodium chloride being especially preferred. Preferably, they should make up at least 60% by weight of the total composition.

Preferably the weight ratio of particulate carrier to water-soluble salt is from 1:1 to 1:20, more preferably from 1:5 to 1:20, even more preferably from 1:10 to 1:20 and most preferably from 1:8 to 1:15. In addition, the ratio of water-soluble salt to perfume is preferably from 20:1 to 1.5:1, more preferably from 8:1 to 5:1 or from 10:1 to 20:1

A typical composition according to this invention will have 80% salt, 10% silica and 10% fragrance. This is in marked contrast to the 50-70% silica and 30-50% fragrance in typical known formulations.

In addition to the essential components mentioned hereinabove, the fragrance-providing compositions according to the invention may additionally contain other known ingredients added in art-recognised quantities to perform their known functions. One such particularly useful ingredient is clay, added to give a softening effect. Particularly preferred clays are bentonites. Examples of other art-recognised ingredients that can be included are antibacterial agents, fluorescing and whitening agents and malodour counteracting agents.

The fragrance-providing compositions according to the invention are prepared by thoroughly mixing the dry ingredients (particulate carrier, salt, other ingredients) and then adding the liquid fragrance composition and stirring until a free-flowing dry powder is achieved. Given that the final product is a free-flowing powder, a wide variety of proportions of ingredients may be used, depending upon the individual natures of the ingredients, and the skilled person can easily determine appropriate amounts by simple experimentation in every case.

The fragrance-providing compositions of the invention are easily made and storage stable. The process for their manufacture is simple and does not suffer from the high rate of fragrance loss that plagues other encapsulation techniques. In a wash or rinse liquor, the water-soluble salt dissolves readily, unlike many known compositions, and the released fragrance partitions preferably on to the substrate being washed. The invention therefore provides a method of applying a fragrance as hereinabove described, to a substrate during washing or rinsing, comprising the adding to the wash or rinse water of a fragrance-providing composition The invention is further described with reference to the following non-limiting examples.

EXAMPLE 1

Admixtures A-H of the compositions shown in Table 1 below are prepared by blending fumed silica, CMC and sodium chloride and then adding perfume, and mixing until a free-flowing powder is achieved. 0.5 g of each is added to one liter of water to give a liquor. A towel is soaked in the liquor for ten minutes and squeezed and dried in open air.

TABLE 1

| | A | B | C | D | E | F | G | H |
|---|---|---|---|---|---|---|---|---|
| Sunshine (perfume) | 10 | 20 | 10 | 15 | 10 | 20 | 10 | 15 |
| AEROSIL ® 200 | 5 | 10 | | | | | 5 | 5 |
| AEROSIL ® R972 | | | 5 | 10 | 5 | 5 | | |
| Sodium Chloride | 85 | 70 | 85 | 75 | 80 | 70 | 80 | 75 |
| BLANOSE ® Refined CMC | | | | | 5 | 5 | 5 | 5 |
| Total | 100 | 100 | 100 | 100 | 100 | 100 | 100 | 100 |

AEROSIL is a fumed silica (trade mark of Degussa).
"Blanose" is carboxymethyl cellulose (trade mark of Hercules)

Olfactive evaluations are carried at regular intervals of time by an expert panel of evaluators.

Performance Rating:
5 ←----------------------4--------------------3----------------2---------------→
Very strong Strong Fair Weak Very Weak

| Olfactive Evaluation scores | | | | |
|---|---|---|---|---|
| | Day 1 | Day 3 | Day 5 | Day 7 |
| A | 5.0 | 4.6 | 4.0 | 3.1 |
| B | 4.8 | 4.6 | 4.1 | 3.0 |

-continued

| Olfactive Evaluation scores | | | | |
|---|---|---|---|---|
| | Day 1 | Day 3 | Day 5 | Day 7 |
| C | 4.6 | 4.1 | 3.6 | 3.0 |
| D | 4.6 | 4.2 | 3.5 | 2.9 |
| E | 4.8 | 4.3 | 3.2 | 2.8 |
| F | 5.0 | 4.6 | 4.3 | 3.6 |
| G | 4.6 | 3.9 | 3.2 | 2.7 |
| H | 4.8 | 4.1 | 3.5 | 3.1 |

EXAMPLE 2

Example 1 is repeated with compositions J-O as shown in the table below.

| | J | K | L | M | N | O |
|---|---|---|---|---|---|---|
| WaterFall (perfume) | 20 | 30 | 10 | 15 | 10 | 5 |
| AEROSIL ® 200 | 5 | 10 | 5 | 5 | 4 | 5 |
| LAUNDROSIL ® DGA | 5 | 10 | 5 | 15 | 6 | 5 |
| Sodium Sulphate | 70 | 50 | 80 | 65 | 80 | 85 |
| Total | 100 | 100 | 100 | 100 | | 100 |

LAUNDROSIL is a detergent-grade bentonite (trade mark of Süd-Chemie AG)

The results are as follows:

| Olfactive Evaluation scores | | | | |
|---|---|---|---|---|
| | Day 1 | Day 2 | Day 5 | Day 7 |
| J | 5 | 4.6 | 4.4 | 3.8 |
| K | 5 | 4.4 | 4.0 | 3.8 |
| L | 4.6 | 4.0 | 3.4 | 2.9 |

-continued

| Olfactive Evaluation scores | | | | |
|---|---|---|---|---|
| | Day 1 | Day 2 | Day 5 | Day 7 |
| M | 4.5 | 3.9 | 3.6 | 3.2 |
| N | 4.7 | 4.0 | 3.4 | 3.0 |
| O | 4.7 | 3.8 | 3.0 | 2.6 |

The invention claimed is:

1. A method of delivering a fragrance to a substrate during washing or rinsing, comprising:

adding to the wash or rinse water a free-flowing pulverulent solid fragrance-providing composition consisting essentially of a particulate carrier in which is absorbed a fragrance in the form of a liquid or an organic solvent solution, and a water-soluble salt of an alkali or alkaline earth metal, the composition comprising at least 60% by weight of water-soluble salt and not more than 20% by weight of particulate carrier, wherein the particulate carrier is a fine porous fumed silica having a particle size of 2 -15 μM and a BET surface area of from 140 to 550 $M^2$/g, and optionally the particulate carrier also contains up to 50% by weight of other absorbent particulate materials, and wherein the weight ratio of water-soluble salt to fragrance is from 20:1 to 1.5:1.

2. A method according to claim 1, wherein the free-flowing pulverulent solid fragrance-providing composition has been formed by a process which comprises the steps of:

thoroughly blending dry ingredients of the composition which include:

a particulate carrier being a fine porous fumed silica having a particle size of 2-15 μM and a BET surface area of from 140 to 550 $M^2$/g, optionally up to 50% wt. of the fine porous fumed silica is substituted by one or more other absorbent particulate materials;

a water soluble salt, further optionally including one or more further ingredients selected from clay, antibacterial agents, fluorescing agents, whitening agents, and malodour counteracting agents, subsequently adding the fragrance in the form a liquid or an organic solvent solution to the blended dry ingredients under stirring conditions to absorb fragrance into the particulate carrier, and continuing stirring to produce the free-flowing solid fragrance-providing composition.

3. A method according to claim 1, the weight ratio of particulate carrier to water-soluble salt is from 1:1 to 1:20.

4. A method according to claim 3, wherein the weight ratio of particulate carrier to water-soluble salt is from 1:5 to 1:20.

5. A method according to claim 4, the weight ratio of particulate carrier to water-soluble salt is from 1:10 to 1:20.

6. A method according to claim 5, the weight ratio of particulate carrier to water-soluble salt is from 1:8 to 1:15.

7. A method according to claim 1, wherein the weight ratio of water-soluble salt to perfume is from 8:1 to 5:1.

8. A method according to claim 1, wherein the weight ratio of water-soluble salt to perfume is from 10:1 to 20:1.

9. A method according to claim 1, wherein the weight ratio of particulate carrier to water-soluble salt is from 1:5 to 1:20, and the weight ratio of water-soluble salt to perfume is from 8:1 to 5:1.

10. A method according to claim 1, wherein the weight ratio of particulate carrier to water-soluble salt is from 1:5 to 1:20, and, the weight ratio of water-soluble salt to perfume is from 10:1 to 20:1.

11. A method according to claim 1, wherein the composition further comprises one or more ingredients selected from clay, antibacterial agents, fluorescing agents, whitening agents, and malodour counteracting agents.

12. A method according to claim 11, wherein the composition comprises a clay.

13. A method according to claim 12, wherein the clay is a bentonite clay.

14. A method according to claim 1, wherein the fine, porous fumed silica is capable of absorbing 2 -3 times their weight of fragrance.

15. A method according to claim 1, wherein the particulate carrier additionally comprises another absorbent particulate material.

16. A method according to claim 15, wherein the absorbent particulate material is a cellulose derivative material.

17. A method according to claim 16, wherein the cellulose derivative material is carboxymethyl cellulose.

18. A method according to claim 1, wherein the wash or rinse water comprises a surfactant.

* * * * *